US012376906B2

(12) United States Patent
Koh

(10) Patent No.: US 12,376,906 B2
(45) Date of Patent: Aug. 5, 2025

(54) METHOD AND APPARATUS FOR SURGICAL PROCEDURE SIMULATION BASED ON VIRTUAL REALITY

(71) Applicant: Korea University Research and Business Foundation, Seoul (KR)

(72) Inventor: Jae Chul Koh, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 26 days.

(21) Appl. No.: 18/536,546

(22) Filed: Dec. 12, 2023

(65) Prior Publication Data

US 2024/0189036 A1 Jun. 13, 2024

(30) Foreign Application Priority Data

Dec. 13, 2022 (KR) .................. 10-2022-0173794

(51) Int. Cl.
*A61B 34/10* (2016.01)
*G09B 9/00* (2006.01)

(52) U.S. Cl.
CPC ............ *A61B 34/10* (2016.02); *G09B 9/00* (2013.01); *A61B 2034/104* (2016.02); *A61B 2034/105* (2016.02)

(58) Field of Classification Search
CPC ...... A61B 34/10; A61B 2034/104–105; G09B 9/00
See application file for complete search history.

(56) References Cited

U.S. PATENT DOCUMENTS 11,011,077 B2   5/2021  Garcia Kilroy
2014/0370475 A1* 12/2014  Bova .................. G09B 23/285
                                                                434/267
(Continued)

FOREIGN PATENT DOCUMENTS

KR     102011236    8/2019
KR     102235579    4/2021
(Continued)

OTHER PUBLICATIONS

H. Seong et al., "Development of pre-procedure virtual simulation for challenging interventional procedures; an experimental study with clinical application", The Korean Journal of Pain, Published online Oct. 1, 2022, 11 pages.
(Continued)

*Primary Examiner* — Timothy A Musselman
(74) *Attorney, Agent, or Firm* — Loginov & Associates, PLLC; William A. Loginov

(57) ABSTRACT

A method and apparatus for a surgical procedure simulation based on virtual reality (VR) are provided. The method includes generating a virtual three-dimensional (3D) body model corresponding to a body part of a subject of a surgical procedure based on a computed tomography (CT) image and providing a surgical procedure simulation for spinal cord stimulation based on the virtual 3D body model. The providing of the surgical procedure simulation for spinal cord stimulation includes outputting a virtual screen including the virtual 3D body model and a virtual C-arm apparatus, providing a surgical procedure simulation of loss of resistance (LOR) according to a selection of a user wearing the surgical procedure simulation apparatus within the virtual screen, and providing, when the surgical procedure simulation of LOR is completed, a surgical procedure simulation (Continued)

for lead insertion into a virtual spinal cord part included in the virtual 3D body model.

15 Claims, 14 Drawing Sheets

(56) References Cited

U.S. PATENT DOCUMENTS

2017/0372640 A1* 12/2017 Lampotang .............. G09B 9/00
2019/0279524 A1    9/2019 Stoyanov

FOREIGN PATENT DOCUMENTS

| KR | 102240184 | 4/2021 |
| KR | 102289547 | 8/2021 |
| WO | 2022197550 | 9/2022 |

OTHER PUBLICATIONS

Bott, O.J., et al., "virtX—Evaluation of a Computer-based Training System for Mobile C-arm Systems in Trauma and Orthopedic Surgery", Methods Inf Med Mar. 2008, Received Feb. 2, 2007, Accepted Oct. 21, 2007.

\* cited by examiner

METHOD AND APPARATUS FOR SURGICAL PROCEDURE SIMULATION BASED ON VIRTUAL REALITY

CROSS-REFERENCE TO RELATED APPLICATION

This application claims the benefit of Korean Patent Application No. 10-2022-0173794 filed on Dec. 13, 2022, in the Korean Intellectual Property Office, the entire disclosure of which is incorporated herein by reference for all purposes.

BACKGROUND

1. Field of the Invention

One or more embodiments relate to technology of a surgical procedure simulation based on virtual reality (VR).

2. Description of the Related Art

Conventionally, when performing a procedure on patients with difficult anatomical structures due to spinal diseases, considerable costs are incurred. Due to a difficulty and cost issue, it is difficult to train medical staff who perform a procedure/operation on spine-related diseases. To solve this issue, matching technology that implements an apparatus similar to an actual surgical apparatus to perform an operation/procedure in a virtual reality (VR) space and supports an operation/procedure using the apparatus is being developed.

SUMMARY

According to an aspect, there is provided a method for a surgical procedure simulation based on virtual reality (VR), the method including receiving a computed tomography (CT) image of a body part of a subject of a surgical procedure, generating a virtual three-dimensional (3D) body model corresponding to the body part based on the CT image, and providing a surgical procedure simulation for spinal cord stimulation based on the virtual 3D body model. The providing of the surgical procedure simulation for spinal cord stimulation may include outputting a virtual screen including the virtual 3D body model and a virtual C-arm apparatus, providing a surgical procedure simulation of loss of resistance (LOR) using a syringe according to a selection of a user wearing the surgical procedure simulation apparatus within the virtual screen, and providing, when the surgical procedure simulation of LOR is completed, a surgical procedure simulation for inserting a lead into a virtual spinal cord part included in the virtual 3D body model.

According to an aspect, there is provided a surgical procedure simulation apparatus including a memory including instructions and a processor connected to the memory and configured to execute the instructions. When the instructions are executed by the processor, the processor is configured to receive a CT image of a body part of a subject of a surgical procedure, generate a virtual 3D body model corresponding to the body part based on the CT image, provide a surgical procedure simulation for spinal cord stimulation based on the virtual 3D body model, output a virtual screen including the virtual 3D body model and a virtual C-arm apparatus, provide a surgical procedure simulation of loss of resistance using a syringe according to a selection of a user wearing the surgical procedure simulation apparatus within the virtual screen, and provide, when the surgical procedure simulation of LOR is completed, a surgical procedure simulation for lead insertion into a virtual spinal cord part included in the virtual 3D body model.

Additional aspects of embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Figure 1:
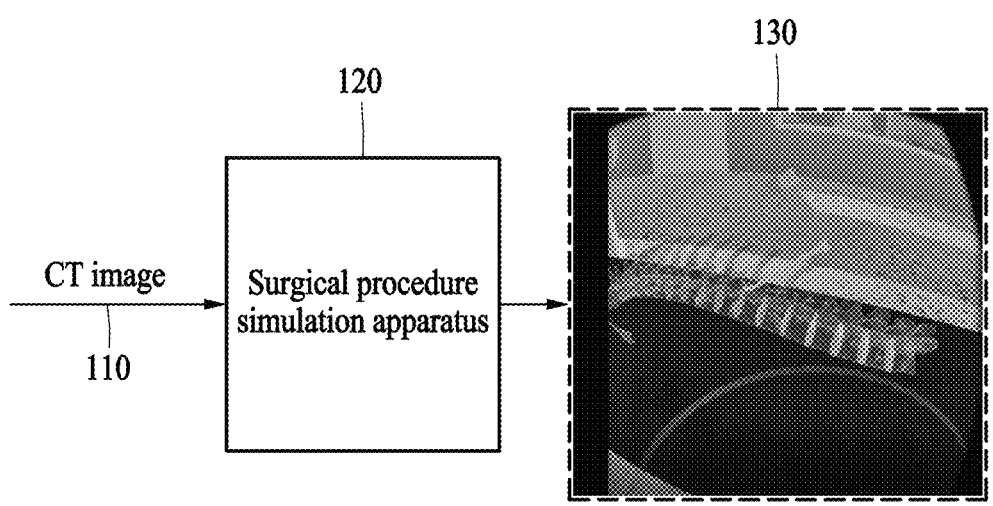
FIG. 1 is a diagram illustrating an overview of a system that provides a surgical procedure simulation, according to an embodiment.

The following detailed structural or functional description is provided as an example only and various alterations and modifications may be made to embodiments. Thus, an actual form of implementation is not construed as limited to the embodiments described herein and should be understood to include all changes, equivalents, and replacements within the idea and the technical scope of the disclosure.

Although terms such as first, second, and the like are used to describe various components, the components are not limited to the terms. These terms should be used only to distinguish one component from another component. For example, a first component may be referred to as a second component, and similarly the second component may also be referred to as the first component.

It should be noted that if one component is described as being "connected," "coupled," or "joined" to another component, the first component may be directly connected, coupled, or joined to the second component, or a third component may be "connected," "coupled," or "joined" between the first and second components.

The singular forms "a," "an," and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which the present disclosure pertains. Terms such as those defined in commonly used dictionaries are to be interpreted as having a meaning that is consistent with their meaning in the context of the relevant art and are not to be interpreted in an idealized or overly formal sense unless expressly so defined herein.

Hereinafter, the embodiments are described in detail with reference to the accompanying drawings. When describing the embodiments with reference to the accompanying drawings, like reference numerals refer to like components and a repeated description related thereto is omitted.

A system that provides a surgical procedure simulation described in this specification may generate a three-dimensional (3D) model based on a two-dimensional (2D) computed tomography (CT) image, generate a virtual surgical apparatus that can be manipulated by a user, and generate a virtual X-ray image in which a virtual surgical apparatus (e.g., a lead) is shown by irradiating virtual X-rays on the 3D model in which a virtual surgical apparatus (e.g., a lead) is inserted, thereby providing an interface for a surgical procedure simulation. The user (or medical staff or an operator performing a surgical procedure) may manipulate the virtual surgical apparatus at the user's discretion through the interface for a surgical procedure simulation and determine an optimal path for the surgical procedure based on the 3D model and an image of the virtual surgical apparatus displayed in the virtual X-ray image. Using the system, the user may record information on an angle, gradient, position, and the like of a virtual radiation imaging apparatus that generates the virtual X-ray image while the surgical procedure is being performed using the determined optimal path and ensure that the surgical procedure may be performed in the same environment using the optimal path, in an actual surgical procedure situation. A surgical procedure described herein may include or be substituted by a procedure, an operation, and other treatment methods.

FIG. 1 is a diagram illustrating an overview of a system that provides a surgical procedure simulation, according to an embodiment.

Referring to FIG. 1, a surgical procedure simulation apparatus 120 may receive a CT image 110. The surgical procedure simulation apparatus 120 may generate a 3D model based on the CT image 110. The surgical procedure simulation apparatus 120 may generate a virtual X-ray image based on the 3D model. In addition, the surgical procedure simulation apparatus 120 may generate a virtual surgical apparatus. The surgical procedure simulation apparatus 120 may provide an interface 130 for a surgical procedure simulation in which a virtual surgical apparatus and the 3D model are displayed, based on the 3D model and the virtual X-ray image.

Figure 2:
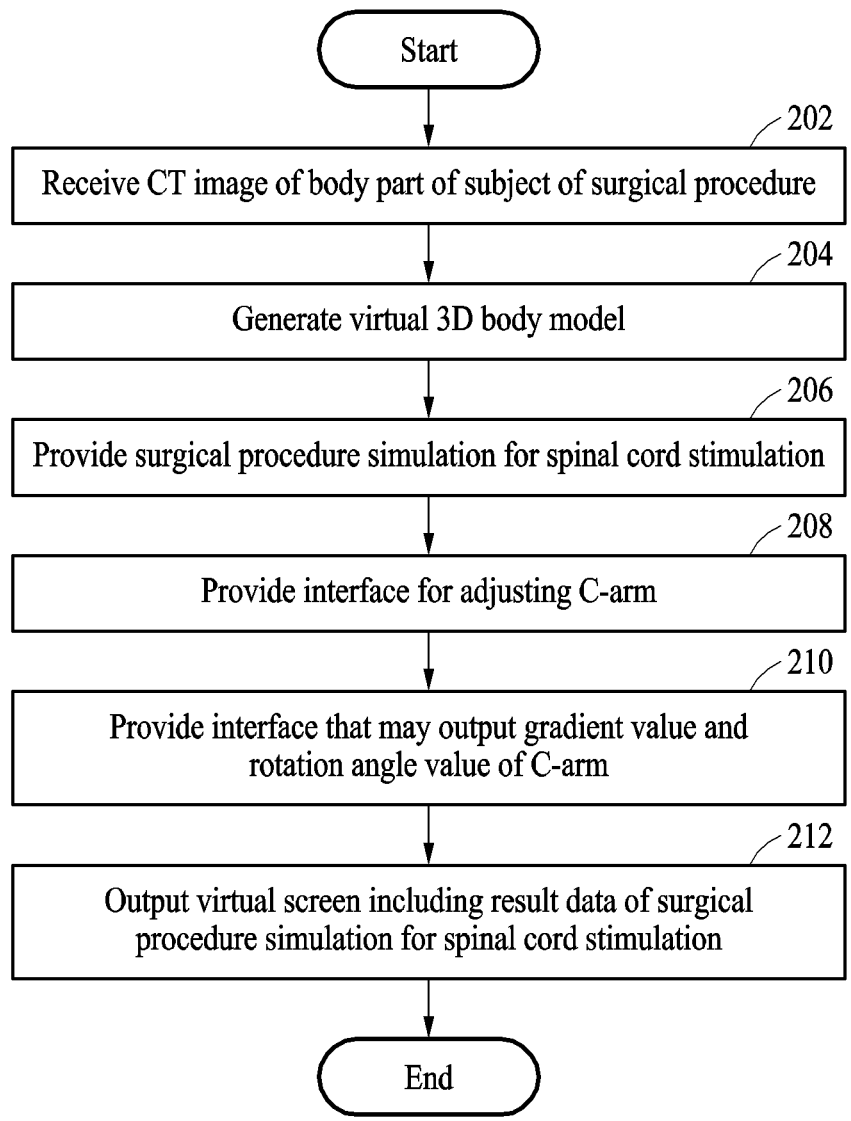
FIG. 2 is a flowchart illustrating a method for a surgical procedure simulation according to an embodiment.

FIG. 2 is a flowchart illustrating a method for a surgical procedure simulation according to an embodiment. For example, operations of the method for a surgical procedure simulation may be performed by the surgical procedure simulation apparatus 120 of FIG. 1.

Referring to FIG. 2, an example of an operation sequence of the method for a surgical procedure simulation is illustrated. However, the operation sequence is not limited thereto, and at least two operations may be performed in parallel. Alternatively, any one of the operations may be omitted.

In operation 202, a surgical procedure simulation apparatus may receive a CT image of a body part of a subject of a surgical procedure. The CT image may be in a 2D form, and the subject of the surgical procedure may refer to a patient with a spine-related disease.

In operation 204, the surgical procedure simulation apparatus may generate a virtual 3D body model corresponding to the body part based on the CT image. The surgical procedure simulation apparatus may generate voxel data of the CT image based on the CT image and generate the virtual 3D body model based on the voxel data. A voxel is a volume element and may be a concept in which a volume is reflected in a pixel. The surgical procedure simulation apparatus may generate the virtual 3D body model from a 2D CT image by performing visualization only for CT images having a Hounsfield units (HU) value of, for example, "200" to "400" and processing the rest of the CT images to be transparent areas. A range of HU values on which visualization is to be performed may be determined based on bone density of the subject of the surgical procedure.

In addition, the surgical procedure simulation apparatus may match the generated virtual 3D body model to a virtual space including a generator that generates virtual X-rays and a sensor that senses the virtual X-rays. For example, the surgical procedure simulation apparatus may place the virtual 3D body model in the virtual space by using an image direction, image position, and interval value of the CT image. The surgical procedure simulation apparatus may locate the CT image in the virtual space based on spatial position information of a digital imaging and communications in medicine (DICOM) file and match the CT image to a virtual space such as 3D polygonal data prepared in advance.

In operation 206, the surgical procedure simulation apparatus may provide a surgical procedure simulation for spinal cord stimulation based on the virtual 3D body model. Since a spinal cord stimulation procedure requires considerable cost in actual treatment, it is difficult to give many opportunities to inexperienced doctors. According to an embodiment, by providing the surgical procedure simulation for spinal cord stimulation, it may be possible to provide an experience close to an actual surgical procedure at a low cost and solve the limitations of only learning through anatomy practice or theoretical education.

The surgical procedure simulation apparatus may provide a surgical procedure simulation of loss of resistance (LOR) using a syringe according to a selection of a user wearing the surgical procedure simulation apparatus. LOR may be a technique for confirming whether a syringe enters a target position in a virtual body part to be treated. A touchy needle may be connected to the syringe. A liquid such as physiological saline or air may be used as a medium in LOR.

When the syringe is inserted into the target position, the user may feel a sense of LOR. The user may check an extent to which the touchy needle is inserted into a body part of the subject of the surgical procedure through a virtual X-ray image.

When the surgical procedure simulation of LOR is completed, the surgical procedure simulation apparatus may provide a surgical procedure simulation for lead insertion into a virtual spinal cord part included in the virtual 3D body model. After completing the surgical procedure simulation of LOR, the user may leave the touchy needle inserted in the body part of the subject of the surgical procedure and remove the syringe. The user may prepare a lead to be inserted into the body part of the subject of the surgical procedure. The user may insert the lead through the touchy needle inserted in the body part of the subject of the surgical procedure. The surgical procedure simulation apparatus may generate a virtual X-ray image indicating a degree to which the lead is inserted into the virtual spinal cord part. The surgical procedure simulation apparatus may output the virtual X-ray image indicating the degree to which the lead is inserted into the virtual spinal cord part to a virtual monitor included in a virtual C-arm apparatus. This is described in detail with reference to FIG. 10 below.

The user may adjust the degree to which the lead is inserted into the virtual spinal cord part through the virtual X-ray image that is output on the virtual monitor. The surgical procedure simulation apparatus may provide an interface for adjusting a direction of the lead insertion. This is described in detail with reference to FIG. 11 below.

In operation 208, the surgical procedure simulation apparatus may provide an interface for adjusting a C-arm. The user may adjust a gradient or a rotation angle of the C-arm through the interface. The user may observe the lead inserted into the body part of the user from various angles by adjusting the gradient or the rotation angle of the C-arm.

In operation 210, the surgical procedure simulation apparatus may provide an interface that may output a gradient value and a rotation angle value of the C-arm. The user may finely adjust the gradient and the rotation angle of the C-arm through the interface. A detailed description of this is given with reference to FIG. 12.

In operation 212, the surgical procedure simulation apparatus may output a virtual screen including result data of the surgical procedure simulation for spinal cord stimulation. The user may determine whether the user himself/herself has performed spinal cord stimulation properly through the virtual screen including the result data of the surgical procedure simulation for spinal cord stimulation.

Figure 3:
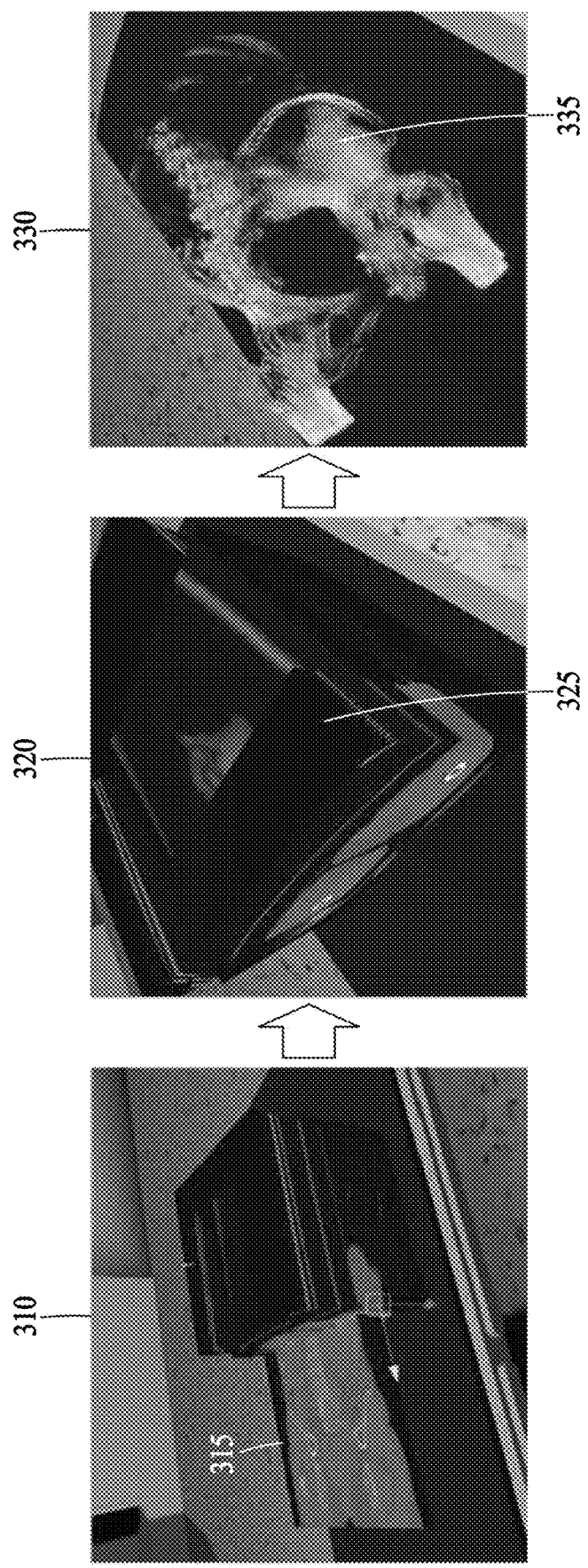
FIG. 3 is a flowchart illustrating a process of generating a three-dimensional (3D) model from a computed tomography (CT) image according to an embodiment.

FIG. 3 is a flowchart illustrating a process of generating a 3D model from a CT image according to an embodiment; The embodiment of FIG. 3 may correspond to operation 204 of the detailed description of FIG. 2. In operation 310, the surgical procedure simulation apparatus may place a CT image 315 in a 2D form in the virtual space. In operation 320, the surgical procedure simulation apparatus may generate a stereoscopic image 325 from the CT image 315. In operation 330, the surgical procedure simulation apparatus may generate a 3D model 335 by performing visualization only for CT images having an HU value within a predetermined range.

Figure 4:
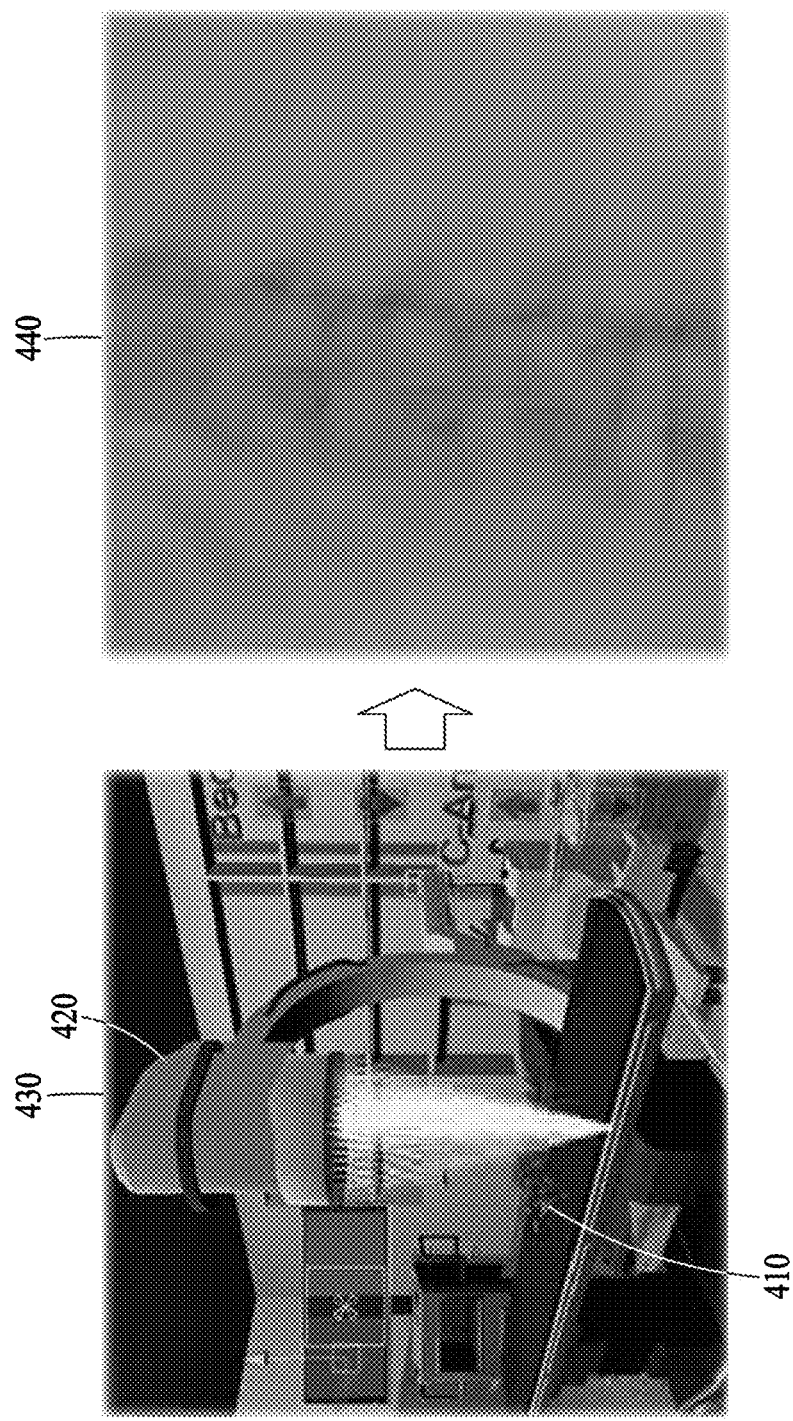
FIG. 4 is a flowchart illustrating a process of generating a virtual X-ray image, according to an embodiment.

FIG. 4 is a flowchart illustrating a process of generating a virtual X-ray image, according to an embodiment.

In operation 430, a 3D model 410 and a virtual radiation imaging apparatus 420 may be located in a virtual space. The virtual radiation imaging apparatus 420 may radiate X-rays to the 3D model 410 at a position, gradient, and direction determined to be suitable for radiating X-rays to the 3D model 410 based on a predetermined criterion. In response to this, in operation 440, the surgical procedure simulation apparatus may generate a virtual X-ray image.

Figure 5:
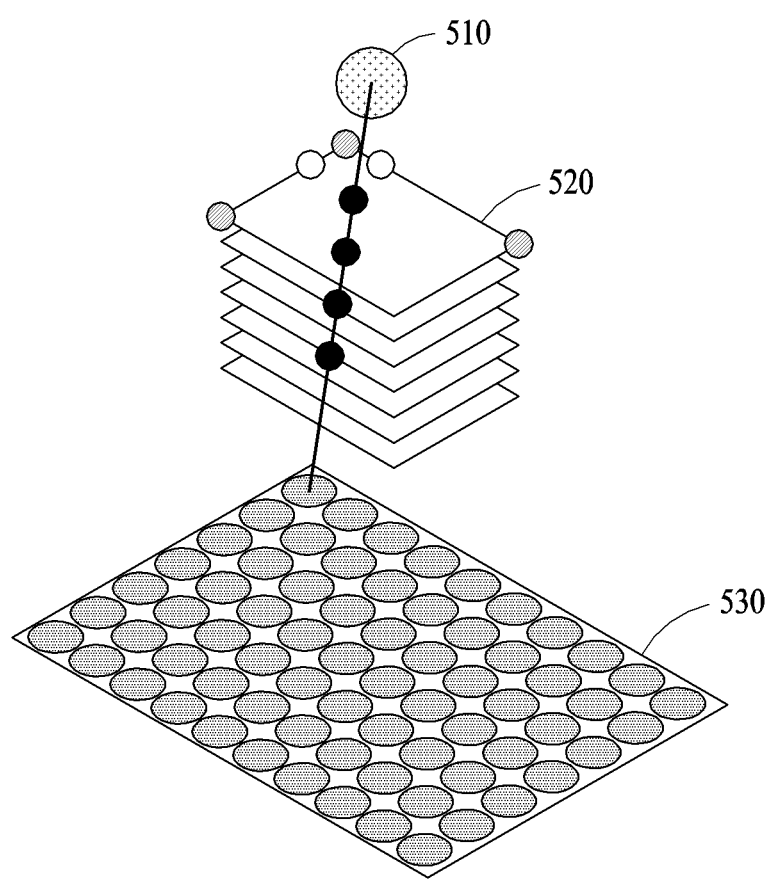
FIG. 5 is a diagram illustrating a process of generating a virtual X-ray image, according to an embodiment.

FIG. 5 is a diagram illustrating a process of generating a virtual X-ray image, according to an embodiment.

Referring to FIG. 5, the reference numeral 510 may indicate a generator for generating virtual X-rays, and the reference numeral 530 may indicate a sensor. The reference numeral 520 may indicate a 3D model including a plurality of data slices. The generator 510, the sensor 530, and the 3D model 520 may be virtual components arranged in the virtual space.

The generator 510 may generate virtual X-rays and radiate the virtual X-rays to the 3D model 520, and the sensor 530 may sense the virtual X-rays radiated to the 3D model 520. The surgical procedure simulation apparatus may determine at least one point on which the virtual X-rays meet the data slices in the 3D model 520 based on the virtual X-rays sensed by the sensor 530. The surgical procedure simulation apparatus may generate a virtual X-ray image by imaging the point.

Figure 6:
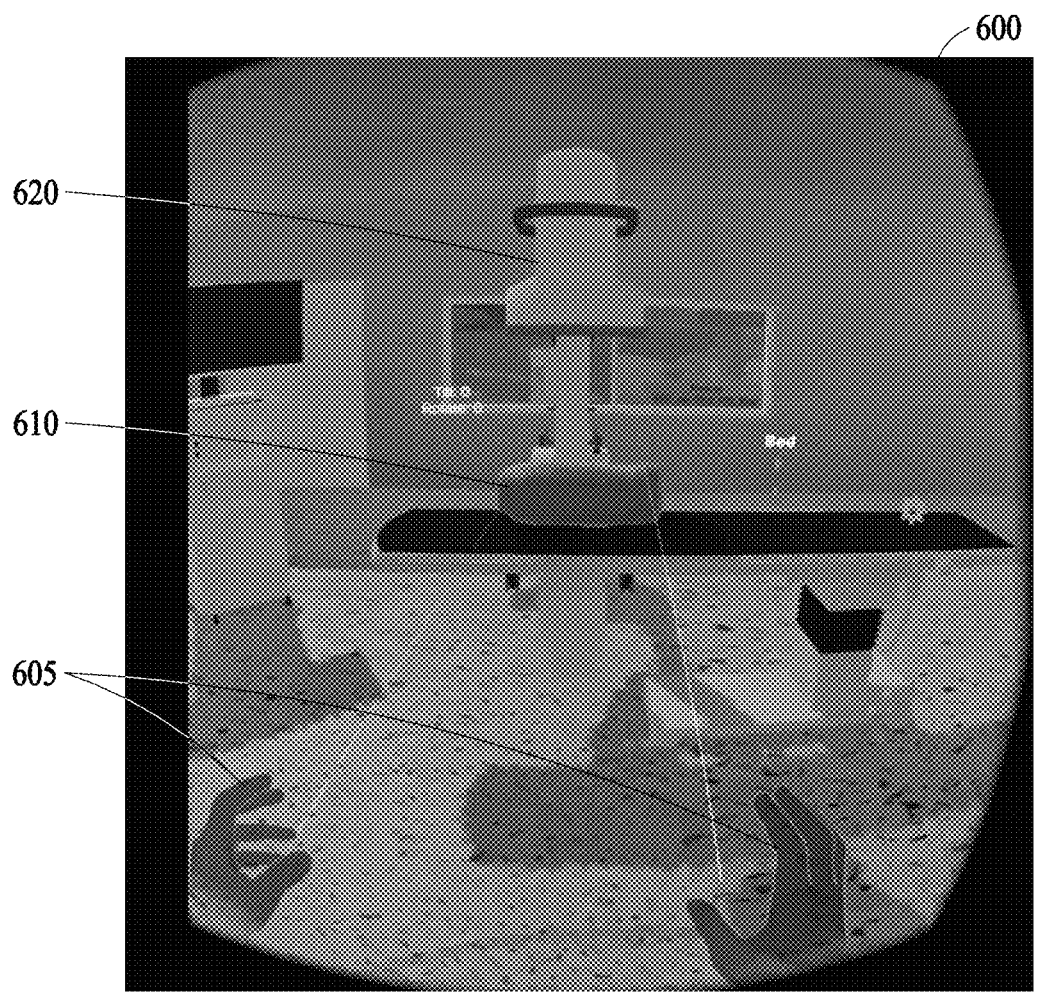
FIG. 6 is a diagram illustrating a surgical procedure simulation for spinal cord stimulation according to an embodiment.

FIG. 6 is a diagram illustrating a surgical procedure simulation for spinal cord stimulation according to an embodiment.

Referring to FIG. 6, a surgical procedure simulation apparatus (e.g., the surgical procedure simulation apparatus 120 of FIG. 1) may output a virtual screen 600 including a virtual 3D body model 610 and a virtual C-arm apparatus 620. A user wearing the surgical procedure simulation apparatus may see a virtual hand 605 displayed on the virtual screen 600. The virtual hand 605 may respond according to an actual hand motion of the user. The user may proceed with the surgical procedure simulation through various interfaces using the virtual hand 605. For example, the user may adjust the height of a bed on which the virtual 3D body model 610 is placed using the virtual hand 605.

Figure 7:
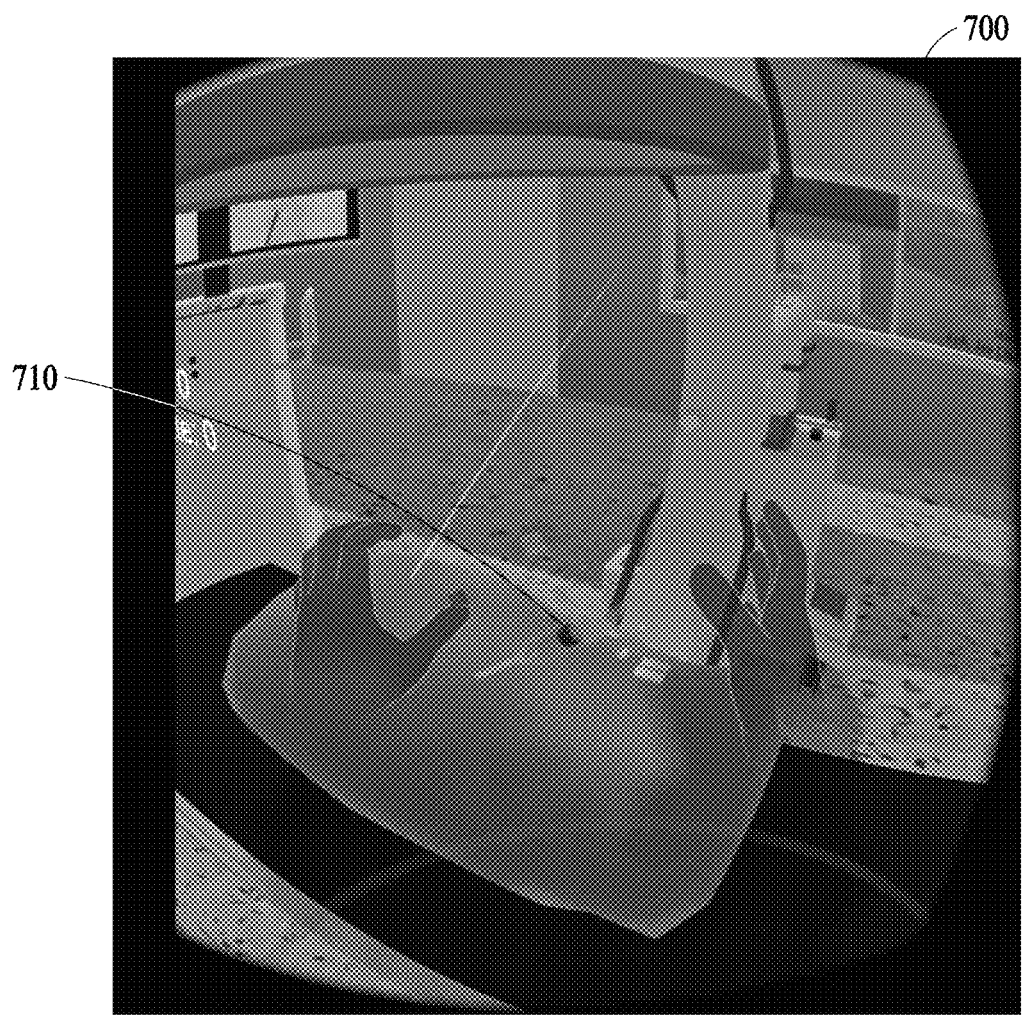
FIG. 7 is a diagram illustrating a surgical procedure simulation of loss of resistance (LOR) using a syringe according to an embodiment.

FIG. 7 is a diagram illustrating a surgical procedure simulation of LOR using a syringe according to an embodiment.

Referring to FIG. 7, a surgical procedure simulation apparatus (for example, the surgical procedure simulation apparatus 120 of FIG. 1) may provide a surgical procedure simulation 700 using a syringe 710 according to the user wearing the surgical procedure simulation apparatus within the virtual screen 600 of FIG. 6. The user may insert the syringe 710 into a virtual body part of a subject of a surgical procedure, using a virtual hand. The syringe 710 may be connected to a touchy needle.

The surgical procedure simulation apparatus may provide an interface for adjusting an insertion direction of the syringe. The interface may provide a virtual button that allows controlling the insertion direction of the syringe to be up, down, left, or right. The user may perform LOR while adjusting the insertion direction of the syringe through the interface for adjusting the insertion direction of the syringe.

Figure 8:
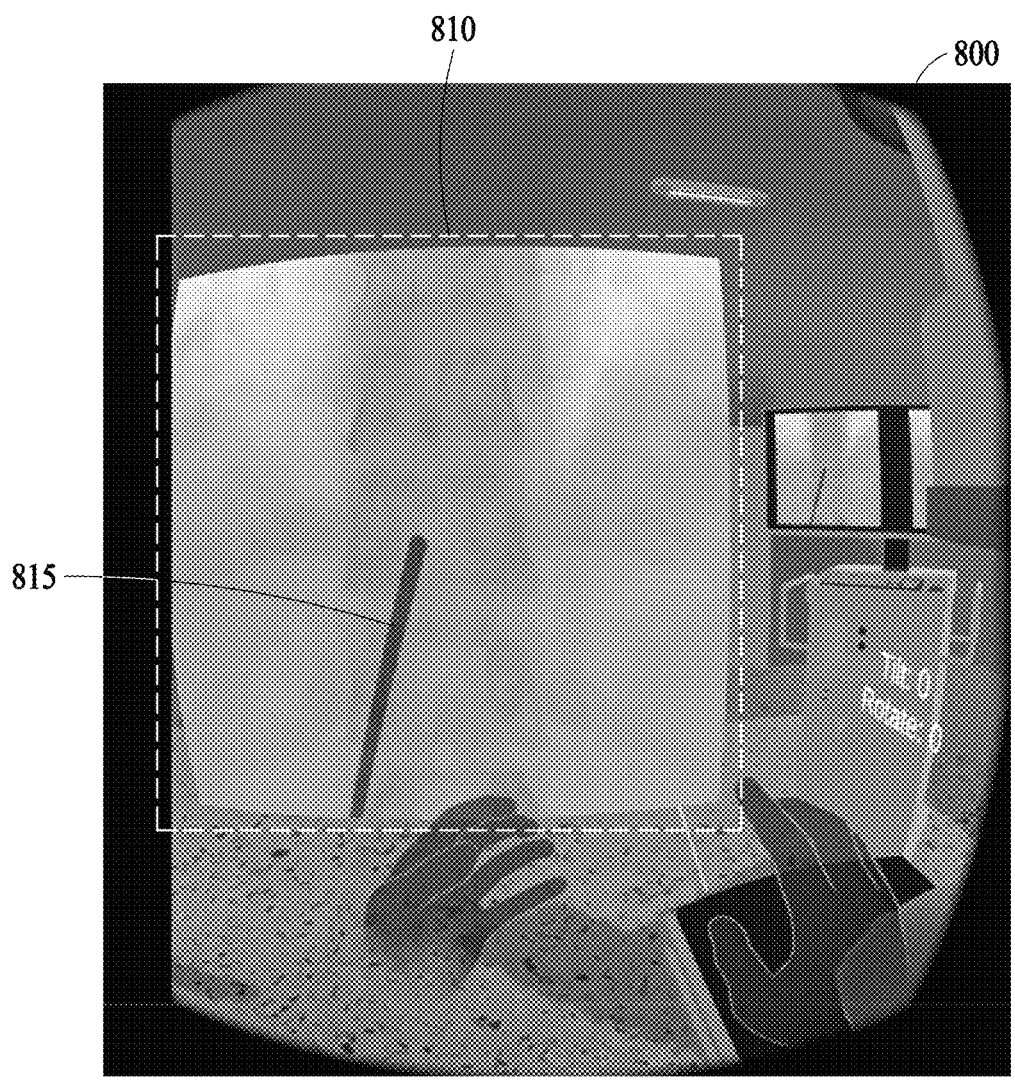
FIG. 8 is a diagram illustrating a virtual X-ray image indicating a degree to which a touchy needle is inserted into a virtual spinal cord part according to an embodiment.

FIG. 8 is a diagram illustrating a virtual X-ray image indicating a degree to which a touchy needle is inserted into a virtual spinal cord part according to an embodiment.

Referring to FIG. 8, a procedure simulation device (for example, the surgical procedure simulation apparatus 120 of FIG. 1) may provide the virtual X-ray image indicating the degree to which the touchy needle connected to a syringe is inserted into a virtual spinal cord part of a subject of a surgical procedure. The user may check whether the touchy needle connected to the syringe is properly inserted into the virtual spinal cord part of the subject of the surgical procedure through the virtual X-ray image. When adjusting an insertion direction of the syringe, the user may refer to the virtual X-ray image indicating the degree to which the touchy needle is inserted.

Figure 9:
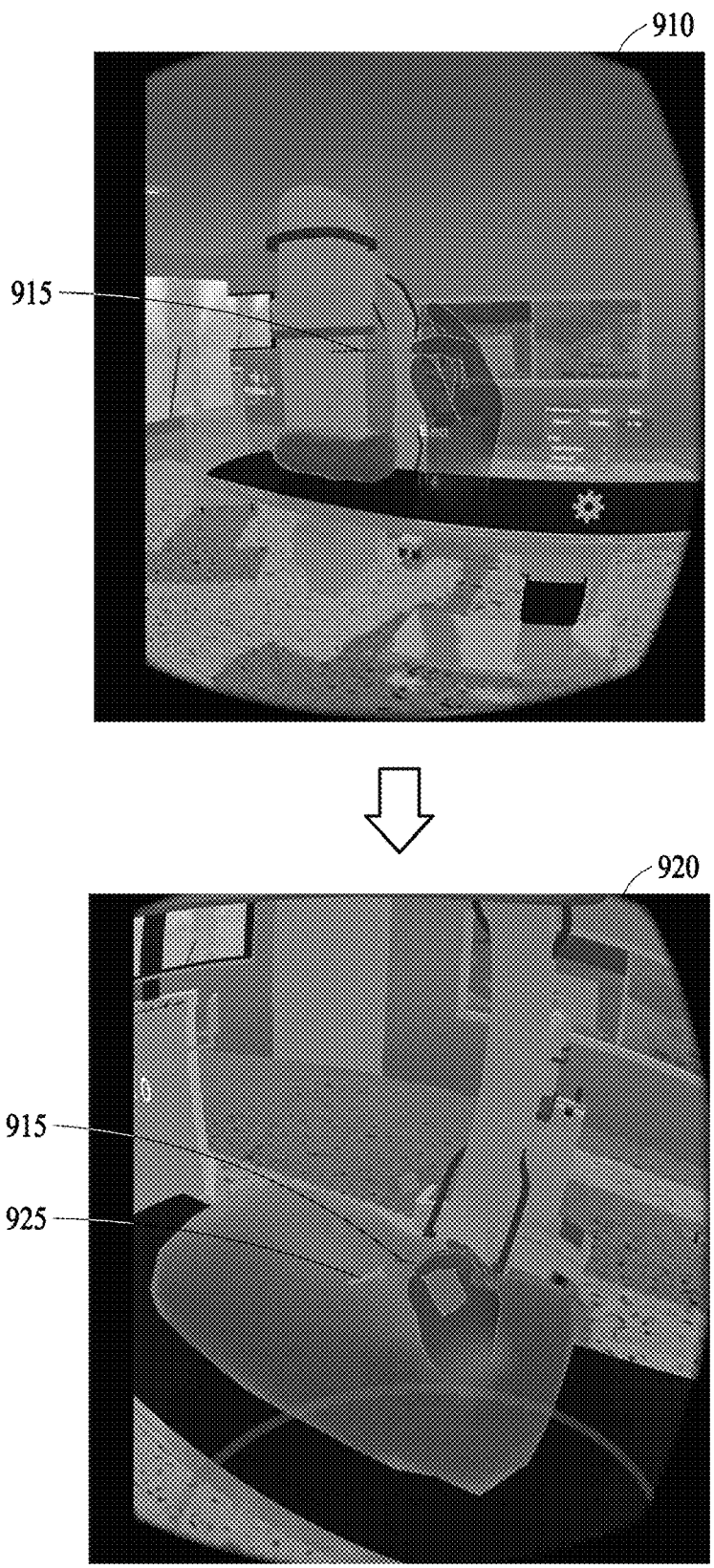
FIG. 9 is a diagram illustrating an operation of inserting a lead into a virtual spinal cord part, according to an embodiment.

FIG. 9 is a diagram illustrating an operation of inserting a lead into a virtual spinal cord part, according to an embodiment.

Referring to FIG. 9, when a surgical procedure simulation of LOR is completed, a surgical procedure simulation apparatus (e.g., the surgical procedure simulation apparatus 120 of FIG. 1) according to an embodiment may provide surgical procedure simulations 910 and 920 for lead insertion into a virtual spinal cord part included in a virtual 3D body model.

In the surgical procedure simulation 910, the user may prepare a lead 915 to be inserted into the virtual spinal cord part included in the virtual 3D body model. In the surgical procedure simulation 920, the user may insert the lead 915 through a touchy needle 925 inserted in the virtual spinal cord part included in the virtual 3D body model.

Figure 10:
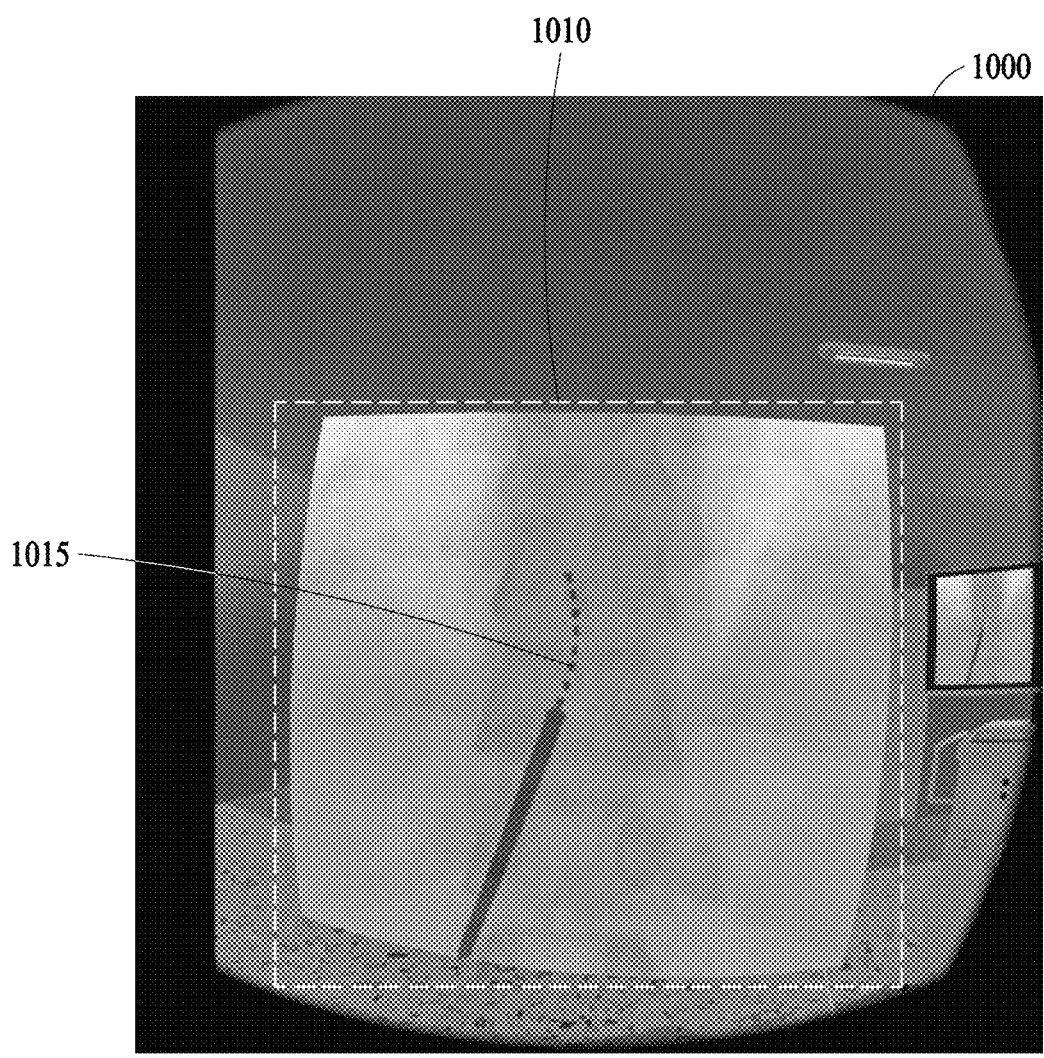
FIG. 10 is a diagram illustrating a virtual X-ray image indicating a degree to which a lead is inserted into a virtual spinal cord part according to an embodiment.

FIG. 10 is a diagram illustrating a virtual X-ray image indicating a degree to which a lead is inserted into a virtual spinal cord part according to an embodiment.

Referring to FIG. 10, a surgical procedure simulation apparatus according to an embodiment may generate a virtual X-ray image 1010 displaying a degree to which the lead is inserted into the virtual spinal cord part on a virtual screen 1000. The surgical procedure simulation apparatus may output the virtual X-ray image 1010 indicating the degree to which a lead 1015 is inserted into the virtual spinal cord part to a virtual monitor included in the virtual C-arm apparatus. The user may check the degree to which the lead is inserted into the virtual spinal cord part on the virtual X-ray image 1010 that is output on the virtual monitor.

Figure 11:
FIG. 11 is a diagram illustrating a surgical procedure simulation for lead insertion into a virtual spinal cord part, according to an embodiment.

FIG. 11 is a diagram illustrating a surgical procedure simulation for lead insertion into a virtual spinal cord part, according to an embodiment.

Referring to FIG. 11, a surgical procedure simulation apparatus according to an embodiment may provide an interface 1110 for adjusting a direction of the lead insertion through a virtual screen 1100 when providing the surgical procedure simulation for lead insertion. The user may adjust the direction of the lead insertion by clicking on the interface 1110 with a virtual hand.

Figure 12:
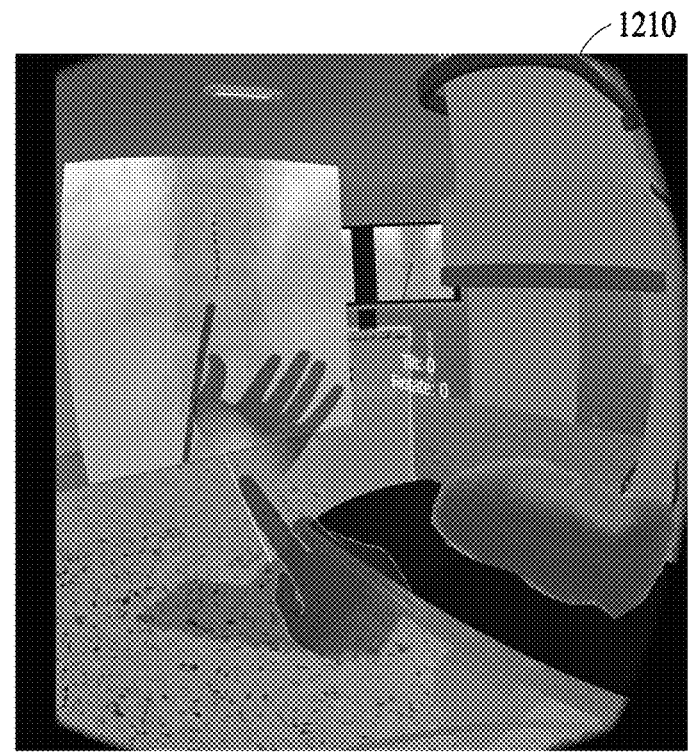
FIG. 12 is a diagram illustrating an interface for adjusting a C-arm according to an embodiment.
Figure 12:
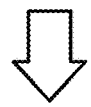
Figure 12:
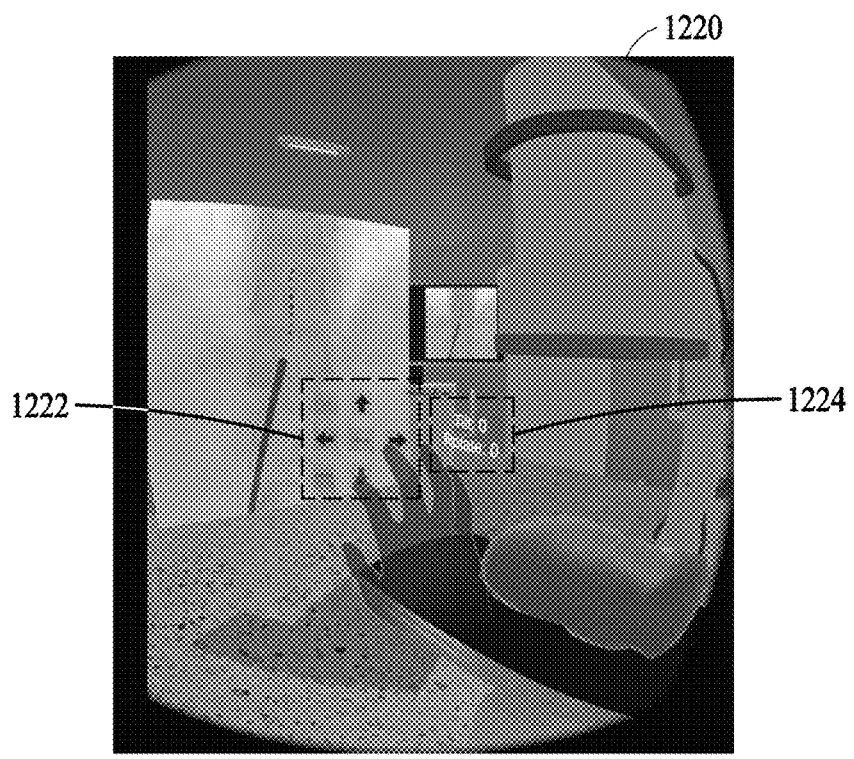

FIG. 12 is a diagram illustrating an interface for adjusting a C-arm according to an embodiment.

Referring to virtual screens 1210 and 1220 of FIG. 12, a surgical procedure simulation apparatus according to an embodiment may output an interface 1222 for adjusting the C-arm, based on a hand motion of a user wearing the surgical procedure simulation apparatus. Referring to the virtual screen 1210, the user wearing the surgical procedure simulation apparatus may perform the hand motion to output the interface 1222 for adjusting the C-arm. For example, the hand motion may be a motion of tapping the left wrist twice with a finger of the right hand. Hand motions to output the interface 1222 may vary according to embodiments.

Referring to the virtual screen 1220, the user performing the hand motion may be provided with the interface 1222 for adjusting the C-arm. The user may adjust a gradient and a rotation angle of the C-arm through the interface 1222. The surgical procedure simulation apparatus may provide an interface 1224 that may output a gradient value and a rotation angle value of the C-arm. The user may adjust the gradient and the rotation angle of the C-arm while checking the gradient value and the rotation angle value of the C-arm through the interface 1224.

Figure 13:
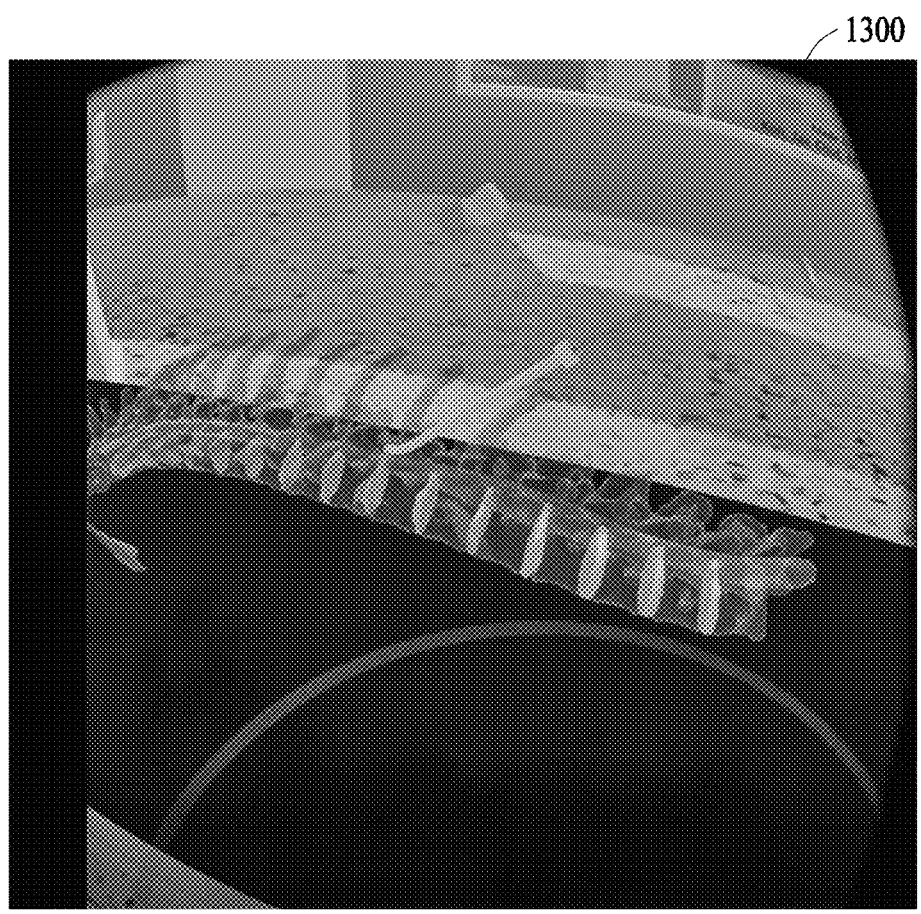
FIG. 13 is a diagram illustrating a virtual screen including result data of a surgical procedure simulation for spinal cord stimulation according to an embodiment.

FIG. 13 is a diagram illustrating a virtual screen including result data of a surgical procedure simulation for spinal cord stimulation according to an embodiment.

Referring to FIG. 13, when a surgical procedure simulation for lead insertion is completed, a surgical procedure simulation apparatus according to an embodiment may output a virtual screen 1300 including result data of the surgical procedure simulation for spinal cord stimulation. The user may evaluate and determine whether the surgical procedure simulation for spinal cord stimulation has been properly performed through the virtual screen 1300.

Figure 14:
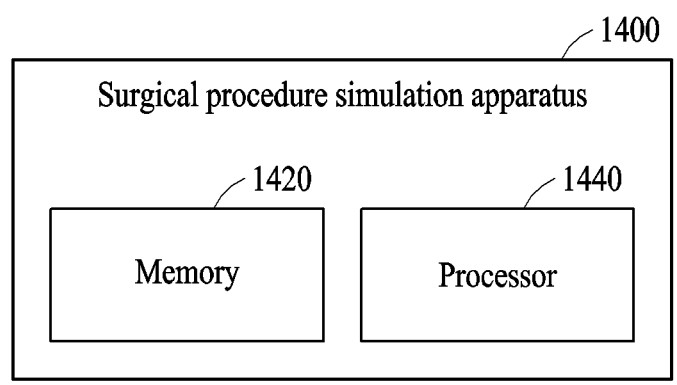
FIG. 14 is a diagram illustrating a configuration of a surgical procedure simulation apparatus according to an embodiment.

FIG. 14 is a diagram illustrating a configuration of a surgical procedure simulation apparatus according to an embodiment.

Referring to FIG. 14, a surgical procedure simulation apparatus 1400 according to an embodiment may include a memory 1420 and a processor 1440.

The memory 1420 may store a variety of data used by at least one component (e.g., the processor 1440) of the surgical procedure simulation apparatus 1400. For example, the memory 1420 may store at least one medical image received from the outside (e.g., a user) and may store intermediate or result data of the medical image processed by the processor 1440.

The memory 1420 may store instructions (or programs) executable by the processor 1440. For example, the instructions may include instructions for performing an operation of the processor 1440 and/or an operation of each component of the processor 1440.

The processor 1440 may execute a program to control at least one other component of the surgical procedure simulation apparatus 1400 connected to the processor 1440 and may perform various data processing, operations, or instructions triggered by the processor 1440. The processor 1440 may store, in the memory 1420, instructions or data received from at least one other component, process the instructions or data stored in the memory 1420, and store result data in the memory 1420.

An operation performed by the processor 1440 may be substantially the same as the operation of the surgical procedure simulation apparatus described above with reference to FIGS. 1 to 13.

In an embodiment, the processor 1440 may receive a CT image of a body part of a subject of a surgical procedure, generate a virtual 3D body model corresponding to the body part based on the CT image, provide a surgical procedure simulation for spinal cord stimulation based on the virtual 3D body model, output a virtual screen including the virtual 3D body model and a virtual C-arm apparatus, provide a surgical procedure simulation of LOR using a syringe according to a selection of a user wearing the surgical procedure simulation apparatus within the virtual screen, and provide, when the surgical procedure simulation of LOR is completed, a surgical procedure simulation for lead insertion into a virtual spinal cord part included in the virtual 3D body model.

In an embodiment, the processor 1440 may provide an interface for adjusting an insertion direction of the syringe.

In an embodiment, the processor 1440 may generate a virtual X-ray image indicating a degree to which the lead is inserted into the virtual spinal cord part and output the virtual X-ray image to a virtual monitor included in the virtual C-arm apparatus.

In an embodiment, the processor 1440 may provide an interface for adjusting a direction of the lead insertion.

In an embodiment, the processor 1440 may output an interface for adjusting a C-arm based on a hand motion of the user.

In an embodiment, the processor 1440 may provide an interface that may output a gradient value and a rotation angle value of the C-arm.

In an embodiment, when the surgical procedure simulation for lead insertion is completed, the processor 1440 may output a virtual screen including result data of the surgical procedure simulation for spinal cord stimulation.

The components described in the embodiments may be implemented by hardware components including, for example, at least one digital signal processor (DSP), a processor, a controller, an application-specific integrated circuit (ASIC), a programmable logic element, such as a field programmable gate array (FPGA), other electronic devices, or combinations thereof. At least some of the functions or the processes described in the embodiments may be implemented by software, and the software may be recorded on a recording medium. The components, the functions, and the processes described in the embodiments may be implemented by a combination of hardware and software.

The above-described hardware devices may be configured to act as one or more software modules in order to perform the operations of the above-described examples, or vice versa.

Although the embodiments have been described with reference to the limited drawings, one of ordinary skill in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Therefore, other implementations, other embodiments, and equivalents to the claims are also within the scope of the following claims.

What is claimed is:

1. A method for a surgical procedure simulation based on virtual reality (VR), the method being performed by a surgical procedure simulation apparatus and comprising:
   receiving a computed tomography (CT) image of a body part of a subject of a surgical procedure;
   placing the CT image of the body part in a 2D form into a virtual surgical space;
   generating a stereoscopic image from the CT image of the body part;
   generating a virtual three-dimensional (3D) body model corresponding to the body part from the stereoscopic image based on portions of the CT image having a Hounsfield unit (HU) value within a predetermined range; and
   providing a surgical procedure simulation for spinal cord stimulation based on the virtual 3D body model,
   wherein the providing of the surgical procedure simulation for spinal cord stimulation comprises:
      outputting a virtual screen comprising the virtual 3D body model and a virtual C-arm apparatus;
      virtually radiating virtual x-rays generated with a virtual x-ray generator at the virtual 3D body model configured as a set of data slices of the CT image virtually disposed between the virtual x-ray generator and a virtual x-ray sensor;
      detecting at least one point in the 3D body model at which the virtual x-rays from the virtual x-ray generator meets a portion of the 3D body model based on sensing of the virtual x-rays by the virtual x-ray sensor;
      generating a virtual X-ray image of the body part based on the detecting the at least one point;
      outputting the virtual X-ray image to a virtual monitor included in the virtual C-arm apparatus;
      providing a surgical procedure simulation of loss of resistance (LOR) using a syringe according to a selection of a user wearing the surgical procedure simulation apparatus within the virtual screen; and
      providing, when the surgical procedure simulation of LOR is completed, a surgical procedure simulation for lead insertion into a virtual spinal cord part included in the virtual 3D body model.

2. The method of claim 1, wherein the providing of the surgical procedure simulation of LOR comprises:
   providing an interface for adjusting an insertion direction of the syringe.

3. The method of claim 1, wherein the providing of the surgical procedure simulation for lead insertion comprises:
   generating a virtual X-ray image indicating a degree to which a lead is inserted into the virtual spinal cord part; and
   outputting the virtual X-ray image to a virtual monitor included in the virtual C-arm apparatus.

4. The method of claim 1, wherein the providing of the surgical procedure simulation for lead insertion comprises:
   providing an interface for adjusting a direction of the lead insertion.

5. The method of claim 1, further comprising:
   outputting an interface for adjusting a C-arm based on a hand motion of the user.

6. The method of claim 1, further comprising:
   providing an interface configured to output a gradient value and a rotation angle value of a C-arm.

7. The method of claim 1, further comprising:
   outputting, when the surgical procedure simulation for lead insertion is completed, a virtual screen comprising result data of the surgical procedure simulation for spinal cord stimulation.

8. A non-transitory computer-readable storage medium storing instructions that, when executed by a processor, cause the processor to perform the method of claim 1.

9. A surgical procedure simulation apparatus comprising:
   a memory comprising instructions; and
   a processor connected to the memory and configured to execute the instructions,
   wherein, when the instructions are executed by the processor, the processor is configured to:
      receive a computed tomography (CT) image of a body part of a subject of a surgical procedure;
      place the CT image of the body part in a 2D form into a virtual surgical space;
      generate a stereoscopic image from the CT image of the body part;
      generating a virtual three-dimensional (3D) body model corresponding to the body part from the stereoscopic image based on portions of the CT image having a Hounsfield unit (HU) value within a predetermined range;
      provide a surgical procedure simulation for spinal cord stimulation based on the virtual 3D body model;
      output a virtual screen comprising the virtual 3D body model and a virtual C-arm apparatus;
      virtually radiate virtual x-rays generated with a virtual x-ray generator at the virtual 3D body model configured as a set of data slices of the CT image virtually disposed between the virtual x-ray generator and a virtual x-ray sensor;

detect at least one point in the 3D body model at which the virtual x-rays from the virtual x-ray generator meets a portion of the 3D body model based on sensing of the virtual x-rays by the virtual x-ray sensor;

generate a virtual X-ray image of the body part based on the detecting the at least one point;

output the virtual X-ray image to a virtual monitor included in the virtual C-arm apparatus;

provide a surgical procedure simulation of loss of resistance (LOR) using a syringe according to a selection of a user wearing the surgical procedure simulation apparatus within the virtual screen, and provide, when the surgical procedure simulation of LOR is completed, a surgical procedure simulation for lead insertion into a virtual spinal cord part included in the virtual 3D body model.

10. The apparatus of claim 9, wherein the processor is configured to:
provide an interface for adjusting an insertion direction of the syringe.

11. The apparatus of claim 9, wherein the processor is configured to:
generate a virtual X-ray image indicating a degree to which a lead is inserted into the virtual spinal cord part; and output the virtual X-ray image to a virtual monitor included in the virtual C-arm apparatus.

12. The apparatus of claim 9, wherein the processor is configured to:
provide an interface for adjusting a direction of the lead insertion.

13. The apparatus of claim 9, wherein the processor is configured to:
output an interface for adjusting a C-arm based on a hand motion of the user.

14. The apparatus of claim 9, wherein the processor is configured to:
provide an interface configured to output a gradient value and a rotation angle value of a C-arm.

15. The apparatus of claim 9, wherein the processor is configured to:
output, when the surgical procedure simulation for lead insertion is completed, a virtual screen comprising result data of the surgical procedure simulation for spinal cord stimulation.

* * * * *